(12) United States Patent
Cable, II

(10) Patent No.: US 11,259,915 B2
(45) Date of Patent: Mar. 1, 2022

(54) FLUID-FILLED HAPTIC FOR AN INTRAOCULAR LENS

(71) Applicant: Alcon Inc., Fribourg (CH)

(72) Inventor: Craig Alan Cable, II, Fort Worth, TX (US)

(73) Assignee: Alcon, Inc., Fribourg (CH)

( * ) Notice: Subject to any disclaimer, the term of this patent is extended or adjusted under 35 U.S.C. 154(b) by 96 days.

(21) Appl. No.: 16/227,149

(22) Filed: Dec. 20, 2018

(65) Prior Publication Data

US 2019/0183633 A1 Jun. 20, 2019

Related U.S. Application Data

(60) Provisional application No. 62/608,029, filed on Dec. 20, 2017.

(51) Int. Cl.
*A61F 2/16* (2006.01)
*A61F 2/00* (2006.01)

(52) U.S. Cl.
CPC .............. *A61F 2/16* (2013.01); *A61F 2/1694* (2013.01); *A61F 2002/0081* (2013.01); *A61F 2002/169* (2015.04); *A61F 2002/16901* (2015.04); *A61F 2002/16902* (2015.04); *A61F 2002/16905* (2015.04); *A61F 2230/0065* (2013.01); *A61F 2250/0003* (2013.01); *A61F 2250/0013* (2013.01); *A61F 2250/0063* (2013.01)

(58) Field of Classification Search
CPC .... A61F 2/16; A61F 2/1694; A61F 2002/169; A61F 2002/16901; A61F 2002/16902; A61F 2002/16905; A61F 2002/0081; A61F 2230/0065; A61F 2250/0003; A61F 2250/0013; A61F 2250/0063
See application file for complete search history.

(56) References Cited

U.S. PATENT DOCUMENTS

| | | | |
|---|---|---|---|
| 4,902,293 A | 2/1990 | Feaster | |
| 2010/0204790 A1* | 8/2010 | Whitsett | A61F 2/1613 623/6.39 |
| 2016/0008126 A1* | 1/2016 | Salahieh | A61F 2/1601 623/6.13 |
| 2017/0119521 A1* | 5/2017 | Kahook | A61F 2/1648 |
| 2018/0271645 A1* | 9/2018 | Brady | G02C 7/08 |

FOREIGN PATENT DOCUMENTS

| | | | | |
|---|---|---|---|---|
| EP | 3297574 | * | 3/2018 | ............ A61F 2/16 |
| WO | 2008/108523 A1 | | 9/2008 | |
| WO | 2016/185017 A1 | | 11/2016 | |
| WO | WO-2017096087 A1 | * | 6/2017 | ............ A61F 2/16 |

* cited by examiner

*Primary Examiner* — Jerrah Edwards
*Assistant Examiner* — Tiffany P Shipmon
(74) *Attorney, Agent, or Firm* — Patterson + Sheridan, LLP (57) ABSTRACT

An IOL utilizes a haptic formed as a toroid portion configured to fit into a capsular bag of an aphakic eye of a patient. The toroid portion may be separate from an IOL optic and may include a receiving feature for the IOL optic. The toroid portion may be configured for intraoperative fluid-filling for snug fitting at the equator of the capsular bag, in order to immobilize the IOL optic.

20 Claims, 5 Drawing Sheets

FLUID-FILLED HAPTIC FOR AN INTRAOCULAR LENS

FIELD

The present disclosure relates generally to intraocular lenses (IOL), and more specifically, to a fluid-filled haptic for an IOL.

BACKGROUND

The human eye includes a cornea and a crystalline lens that are intended to focus light that enters the pupil of the eye onto the retina. However, the eye may exhibit various refractive errors which result in light not being properly focused upon the retina, and which may reduce visual acuity. Many interventions have been developed over the years to correct various ocular aberrations. These include spectacles, contact lenses, corneal refractive surgery, such as laser-assisted in situ keratomileusis (LASIK) or corneal implants, and intraocular lenses (IOLs). In particular, IOLs are also used to treat cataracts by replacing the natural diseased crystalline lens of the eye of a patient. During typical cataract surgery, a conventional single piece IOL is inserted into the capsular bag of a patient to replace the natural crystalline lens.

Whether implanted for refractive errors or for cataract treatment, a typical IOL may shift, either rotationally or axially or in combination, within the capsular bag over time, which may negatively impact the patient's quality of vision. Specifically, the exact location of the lens in the eye may determine the type and degree of refractive power achieved. Therefore, an exact position of the IOL in the eye is assumed when calculating a surgical plan for a patient. When the exact position of the IOL deviates from the surgical plan assumptions, refractive errors may be introduced, which is undesirable.

Also, traditional IOLs may suffer from capsule opacification, which can lead to a loss of transparency and a decrease in the quality of vision. Other problems affected by traditional IOL designs may include, but are not limited, to folds in the capsular bag (striae) and fibrosis around the haptics of the IOL as well as the IOL itself.

SUMMARY

In certain embodiments, an IOL haptic includes a toroid portion having an outer diameter, an inner diameter, and an interior volume. The interior volume of the toroid portion may be configured to be filled with a fluid. The IOL haptic may further include a receiving feature on the inner diameter of the toroid portion for receiving an IOL optic.

In certain embodiments, an IOL includes a haptic and an optic. The haptic may include a toroid portion having an outer diameter and an inner diameter and an interior volume configured to be filled with a fluid. The haptic may further include a receiving feature on the inner diameter of the toroid portion for receiving the optic, the optic configured to fit in the receiving feature when the IOL is implanted into an eye of a patient.

In certain embodiments, a method for implanting an IOL includes inserting a haptic of the IOL into an aphakic eye of a patient, the haptic including a toroid portion having an outer diameter and an inner diameter and an interior volume configured to be filled with a fluid. The haptic further includes a receiving feature on the inner diameter of the toroid portion for receiving an IOL optic. The method further includes filling at least a portion of an interior volume with the fluid, and placing the IOL optic in a receiving feature.

BRIEF DESCRIPTION OF THE DRAWINGS

For a more complete understanding of the present invention and its features and advantages, reference is now made to the following description, taken in conjunction with the accompanying drawings, in which.

The skilled person in the art will understand that the drawings, described below, are for illustration purposes only. The drawings are not intended to limit the scope of the applicant's disclosure in any way.

DETAILED DESCRIPTION

The present disclosure relates generally to a fluid-filled haptic for an IOL. The fluid-filled haptic for an IOL disclosed herein may be formed as a fluid-filled toroid that is implanted into the lens capsule and radially exerts pressure against the equator of the capsular bag when filled. The fluid-filled haptic for an IOL disclosed herein may further exert pressure against anterior portions and posterior portions of the capsular bag when filled, in order to aid in anchoring the fluid-filled haptic to the equator of the capsular bag for improved axial and rotational stability. The fluid-filled haptic for an IOL disclosed herein may further maintain a stable and open capsular bag that has been subject to anterior capsulectomy, such as by creation of an anterior capsulorhexis. The fluid-filled haptic for an IOL disclosed herein may also prevent capsular bag opacification, or other negative effects, by keeping the capsular bag open by applying a uniform force around the equator and the posterior capsule. The fluid-filled haptic for an IOL disclosed herein may be implemented as a two piece device comprising a toroid-shaped fluid-filled haptic that receives an IOL optic. The fluid-filled haptic for an IOL disclosed herein may accordingly facilitate postoperative exchange of the IOL optic without affecting the implantation of the fluid-filled haptic.

Figure 1A:
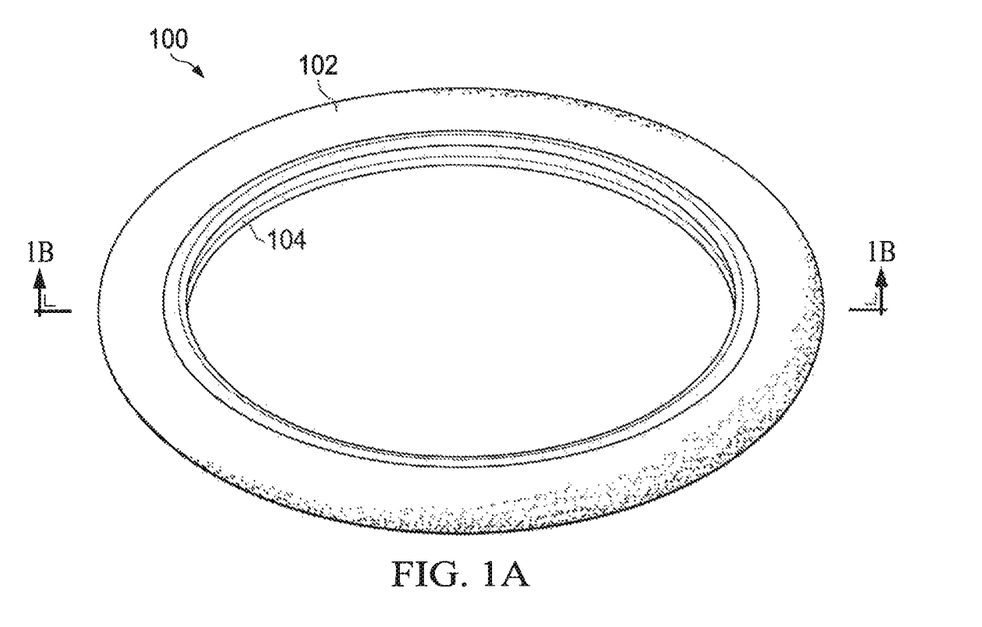
FIGS. 1A and 1B are depictions of a fluid-filled haptic for an IOL.
Figure 1B:
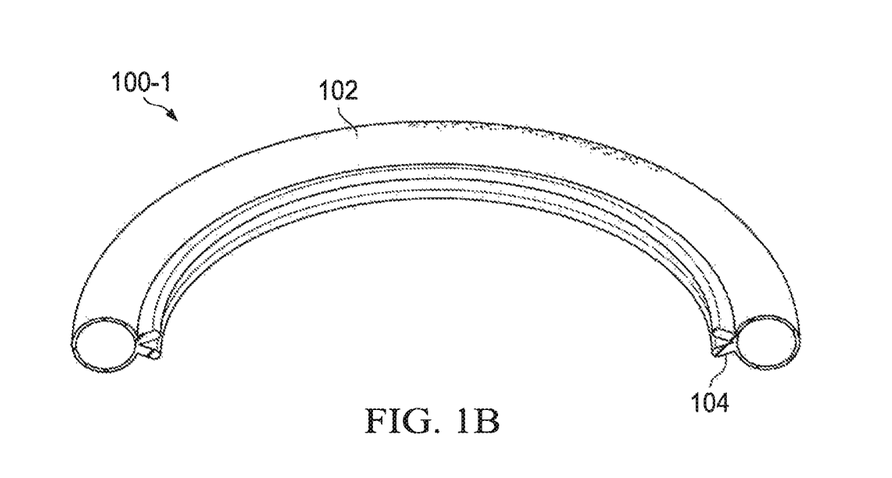

Referring now to the drawings, FIGS. 1A and 1B illustrate an exemplary depiction of a fluid-filled haptic 100 for an IOL. FIGS. 1A and 1B are schematic diagrams for descriptive purposes and are not drawn to scale or perspective. In FIG. 1A, a fluid-filled haptic 100 is shown including a toroid portion 102 and a receiving feature 104 for concentrically retaining an IOL optic (not shown in FIG. 1A) within toroid portion 102. In FIG. 1A, fluid-filled haptic 100 is shown in a filled (or inflated) configuration that corresponds to a post-operative shape within the capsular bag of a patient.

Receiving feature 104 is formed to enable retention of the IOL optic by fluid-filled haptic 100. As visible in the sectional view of a fluid-filled haptic 100-1 in FIG. 1B, receiving feature 104 is shown formed as a circular V-groove that extends from a central inner surface of toroid portion 102. Although receiving feature 104 is shown as the V-groove extending around an entire inner circumference of toroid portion 102 in FIG. 1A for descriptive purposes, it will be understood that receiving feature 104 may be formed using variously shaped structures and elements for retaining the IOL optic, and may be partially formed on the inner circumference, such that receiving feature 104 is absent at certain angular locations on the inner circumference of toroid portion 102. For example, in various implementations, receiving feature 104 may be any one of: a V-groove, a C-groove, a C-channel, one or more magnetic anchors, among others. In particular implementations, receiving feature 104 may be formed with a spring-loaded element (not shown) that secures the IOL optic in the receiving feature 104. For example, the spring-loaded feature may result in an inner diameter of toroid portion 102 being smaller than an outer diameter of the IOL optic.

In certain embodiments, fluid-filled haptic 100 may be injected by a surgeon into the capsular bag in a deflated or empty configuration, which may be suitable, for example, for injection using an injector with a narrow nozzle that can fit in a relatively small corneal incision. After the deflated fluid-filled haptic 100 is inserted into the capsular bag, fluid-filled haptic 100 may then be filled with a fluid to form the shape shown in FIG. 1A. The fluid may be a gas, a liquid, a gel or various combinations thereof, among others. During intraoperative filling of fluid-filled haptic 100, the surgeon may manipulate fluid-filled haptic 100 in order to place and position fluid-filled haptic 100 in a desired orientation within capsular bag, which may be easier to control and manipulate due to the decreased volume of fluid-filled haptic 100 prior to filling. In certain instances, the surgeon may pause and resume the intraoperative filling of fluid-filled haptic 100 in order to give the surgeon improved control during the procedure for precise placement of fluid-filled haptic 100 within the capsular bag.

In some implementations, fluid-filled haptic 100 may have a filling port or a valve to enable filling and draining of the fluid, or components thereof, intraoperatively. For example, receiving feature 104 may be formed of a material that is self-sealing when penetrated by a small injector needle, such as a syringe needle or a blunt needle or a cannula, among others, which are generically referred to herein as a "needle". Accordingly, receiving feature 140 may be formed with sufficient material at the inner circumference to enable self-sealing. In other implementations, a slit that can be penetrated by a needle may be formed on receiving feature 104 to facilitate filling and draining of the fluid. In this manner, receiving feature 104 may be reaccessible to the surgeon to add or remove fluid, as desired, for example to titrate fluid into or out of fluid-filled haptic 100. The titration may involve fluid exchange or introduce another fluid or micro particles into toroid portion 102 of fluid-filled haptic 100.

As noted, the fluid used to fill toroid portion 102 of fluid-filled haptic 100 may be a liquid, a gel, or multiple fluids that interact to result in desired properties. For example, in particular implementations where a hardening or curing of the fluid is desired, a curing agent or an ultraviolet (UV) sensitive material may be used. Certain microparticles may be introduced into the fluid for specific purposes, such as but not limited to a UV blocker, refractive index changing micro particles, among other microparticles. In some implementations, the fluid used to fill fluid-filled haptic 100 may be provided using separate components that are mixed for a desired effect. For example, the fluid used to fill fluid-filled haptic 100 may be provided in two parts, such as a base component and a hardening or curing agent that results in increased stiffness or solidification upon mixing of the two parts, similar to the curing of an epoxy. Even when such a mixture is used for the fluid, fluid-filled haptic 100 may retain a certain degree of flexibility, and may remain more flexible during implantation, but after a certain amount of time the fluid may be cured to be more gel-like or to harden or to solidify to a desired degree, which may be controllable by the selection of the constituent components of the fluid and the mixing protocol. When hardening of the fluid within fluid-filled haptic 100 is used, the hardening may occur as a result of one or more of: a curing/hardening time, a temperature, moisture, exposure to UV light, exposure to laser light, use of a catalyst, among others.

In other implementations, toroid portion 102 of fluid-filled haptic 100 may be directly accessed, rather than using receiving portion 104 as a port, for example when toroid portion 102 is formed using a self-sealing material that enables the surgeon to penetrate through the self-sealing material to fill or drain the fluid or perform the titration techniques mentioned previously.

In various implementations, a material used to form toroid portion 102 of fluid-filled haptic 100 may be flexible to a certain degree, so as to enable expansion and contraction, depending on an interior pressure of the fluid. Such flexibility may also result in an exterior circumferential diameter of toroid portion 102 increasing as the interior pressure of the fluid is increased. Depending on the design and configuration of toroid portion 102 and receiving feature 104, the flexibility may result in the interior circumferential diameter of toroid portion 102 increasing or decreasing as the interior pressure of the fluid is increased. When the interior circumferential diameter decreases with increasing interior pressure, similar to an inner tube of a tire, the circumferential pressure on the IOL optic may increase, which may stabilize the IOL optic in receiving feature 104.

Additionally, as the exterior circumferential diameter of toroid portion 102 increases, fluid-filled haptic 100 may fill the capsular bag towards the equator of the capsular bag, which may stabilize fluid-filled haptic 100 and the IOL optic by tight fitting within the capsular bag, which is desirable. Furthermore, because fluid-filled haptic 100 can be filled in a customized manner for each patient, the expansion of toroid portion 102 to adjust to the equator of the capsular bag enables fluid-filled haptic 100 to be accurately and snugly fitted to different sized capsular bags that occur in any human population, which improves the clinical applicability of fluid-filled haptic 100. The flexibility and expansion exhibited by fluid-filled haptic 100 may allow for a uniform force distribution against the entire equator of the capsular bag when fluid-filled haptic 100 is implanted, which is desirable because of the stabilizing effect for fluid-filled haptic 100 and the IOL optic. The uniform force distribution may also aid in preventing folds in the capsular bag (striae) due to the resulting tension in the capsular bag, which may evenly prevent folding. The action of fluid-filled haptic 100 to keep the capsular bag open by engaging with the capsular bag over the entire external circumference of fluid-filled haptic 100 may aid in prevention of posterior capsular opacification (PCO), also referred to as an "after-cataract". In some implementations, fluid-filled haptic 100 may have a sharpened or square-edged posterior edge (not shown) that engages with the capsular bag in order to improve PCO prevention.

As a result, the design of fluid-filled haptic 100 shown in FIG. 1A may exhibit improved stability in the capsular bag because fluid-filled haptic 100 is anchored to the equator of the bag and may resist being pushed forward by the posterior capsular bag postoperatively, which may provide a high level of axial stability of fluid-filled haptic 100 and the IOL optic. In the case of conventional IOLs without fluid-filled haptic 100, the posterior capsular bag may tend to postoperatively collapse onto the conventional IOL. The design of fluid-filled haptic 100 shown in FIG. 1A may also be rotationally stable, because fluid-filled haptic 100 is in contact with the equator of the capsular bag over the entire external circumference of fluid-filled haptic 100, which resists undesired post operative rotation.

Fluid-filled haptic 100 may also result in a separation between the anterior capsular bag and the posterior capsular bag due to the stability as a result of the uniform force distribution that holds the capsular bag in place. The separation between the anterior capsular bag and the posterior capsular bag, along with the mechanical contact of fluid-filled haptic 100 with various portions of the capsular bag, may aid in keeping the capsular bag open and may aid in preventing PCO of the capsular bag, such as a result of, but not limited to: enhanced endocapsular circulation of aqueous humor into the capsular bag, maintenance of a mechanical barrier to prevent cell migration into or out of the capsular bag, mechanical compression of the capsular bag (keeping the capsular bag pushed open), and maintenance of a postoperative contour of the capsular bag.

As shown in FIG. 1A, fluid-filled haptic 100 may be implemented in a so-called "two-piece" implementation, of which one piece is fluid-filled haptic 100 while the second piece is the IOL optic (not shown in FIG. 1A). The two-piece implementation may facilitate a postoperative exchange of the IOL optic, for example, by preventing opacification of the capsular bag by fibrosis around the IOL optic and by providing a stabile setting of the implanted IOL optic. Since toroid portion 102 may aid in preventing opacification (or at least fibrosis) of the IOL optic, the IOL optic may be anchored solely using receiving feature 104 and may be otherwise freely accessible in the eye. The ease of accessibility of the IOL optic using fluid-filled haptic 100 may allow the surgeon to easily grab and manipulate the IOL optic both during the initial implantation and during a subsequent exchange of the IOL optic. Also, because of the decreased interior circumferential diameter of toroid portion 102, as compared with the diameter of the capsular bag, receiving feature 104 receives an IOL optic having a smaller diameter than the natural lens at the equator of the capsular bag. The reduced diameter of the IOL optic used with fluid-filled haptic 100 may enable the IOL optic to be easier to manipulate intraoperatively and easier to insert and remove from the eye, such as for a subsequent exchange of the IOL optic.

Although the various implementations described above involve filling fluid-filled haptic 100 with a liquid or a gel or a hardened fluid intraoperatively, it is noted that the basic structure of fluid-filled haptic 100 may be implemented without fluid filling. For example, toroid portion 102 may remain hollow (or unfilled) and may be formed using a flexible material that retains a desired shape upon implantation in the capsular bag. possible to have the outside haptic hollow and filled with something other than a liquid. For example, toroid portion 102 may be preoperatively formed, or filled, with a desired agent having desired flexibility and mechanical properties. In various implementations, toroid portion 102 may be comprised of: a gel, an amorphous solid, an epoxy, a thermoplastic material, a composite material, among others and various combinations thereof.

Also in FIG. 1A, receiving feature 104 may receive various kinds of IOL optics used in ophthalmology. For example, fluid-filled haptic 100 may be used with a non-foldable rigid IOL optic, such as comprising a polymethyl methacrylate (PMMA) lens. In some implementations, the IOL optic used with fluid-filled haptic 100 may be a flexible IOL optic, in which the optic zone may be comprised of various materials, such as silicone, hydrophobic acrylic, hydrophilic acrylic, hydrogel, collamer or combinations thereof. As shown, fluid-filled haptic 100 may also be comprised of various materials, such as polypropylene, PMMA, hydrophobic acrylic, hydrophilic acrylic, silicone or combinations thereof.

During implantation of fluid-filled haptic 100 along with the IOL optic into an aphakic eye, various procedures may be performed. First, the natural lens or a previously implanted IOL may be removed to prepare the aphakic eye. Assuming the two-piece implementation, fluid-filled haptic 100 may then be injected into the eye and positioned in the capsular bag, while being filled with a fluid, as described above. For example, a fine needle sized between about 22 to 30 gage may be used to penetrate receiving feature 104 in a self-sealing manner when removed after filling the fluid. In some implementations, the needle may have a blunt tip. The fluid may be selected to have a viscosity of at least 100 centistokes in particular implementations. Then, the IOL optic may be placed within receiving feature 104 after injection into the eye. Once fluid-filled haptic 100 and the IOL optic are implanted, a measuring system may be used for guidance and verification of the position of fluid-filled haptic 100 and the IOL optic. For example, an ORA™ System (Alcon Laboratories Inc., Ft. Worth, Tex.) may be used for spherical, cylinder, and other refractive alignment. In other cases, the measuring system, or optical coherence tomography (OCT) or ultrasound biomicroscopy (UBM) may be used to aid in intraoperative positioning of fluid-filled haptic 100 and the IOL optic. It is noted that the fluid may be removed and refilled intraoperatively as desired for snug fitting and placement of fluid-filled haptic 100 and the IOL optic.

In addition to the two-piece embodiment shown in FIG. 1A and described above, a so-called "one-piece" implementation of an IOL having fluid-filled haptic 100 and incorporating a fixed IOL optic is also contemplated. The one-piece implementation may provide the advantage of shorter and easier implantation effort, due to having a single injection of the IOL (instead of first injecting fluid-filled haptic 100 and then injecting the IOL optic in the two-piece case). Thus, one-piece implementations may reduce surgery time and cost. In the one-piece implementation, the IOL optic, which would be a flexible IOL optic, may be attached using a given number of attachment points (similar to spokes on a wheel) to the interior circumference of toroid portion 102. Then, both toroid portion 102 and the attached flexible IOL optic may be folded together and injected in a single step. The attachment points may be configured for removing the IOL optic subsequently in some implementations, such as by cutting through the attachment points. Because the IOL optic is already fixed to toroid portion 102 in the one-piece implementation, the operative step of placing the IOL optic in receiving feature 104 may be omitted. The one-piece implementation may still be equipped with receiving feature 104 to enable implantation of subsequent IOL optics. In another implementation, toroid portion 102 and the IOL optic may be tethered together and injected using the same injector, and then assembled intraoperatively.

Figure 2A:
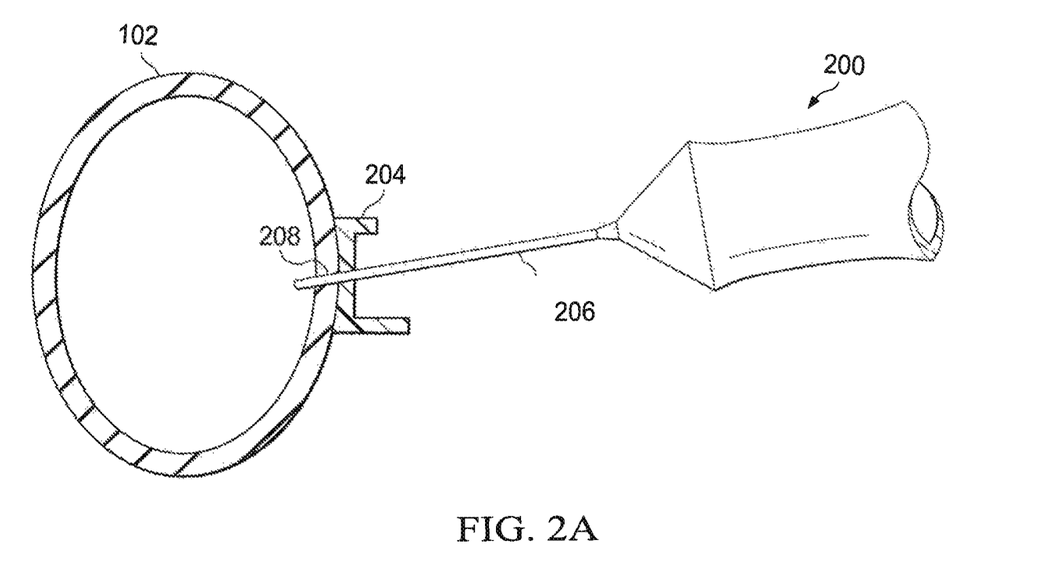
FIGS. 2A, 2B, and 2C are depictions of a fluid-filled haptic for an IOL.

Referring now to FIG. 2A, a fluid-filled haptic 200 is shown above including toroid portion 102 and a receiving feature 204 for concentrically retaining an IOL optic (not shown in FIG. 1A) within toroid portion 102. FIG. 2A is a schematic diagram for descriptive purposes and is not drawn to scale or perspective. FIG. 2A is a sectional view with receiving feature 204 implemented as a C-groove that is self-sealing when a needle 206 penetrates receiving feature 204. Specifically, a needle tip 208 is shown penetrating receiving feature 204 to enable filling of toroid portion 102 with a desired fluid, as described above. The filling of toroid portion 102 shown with fluid-filled haptic 200 may be performed intraoperatively, as desired to fill or inflate toroid portion 102 to a desired fill level or internal pressure.

Figure 2B:
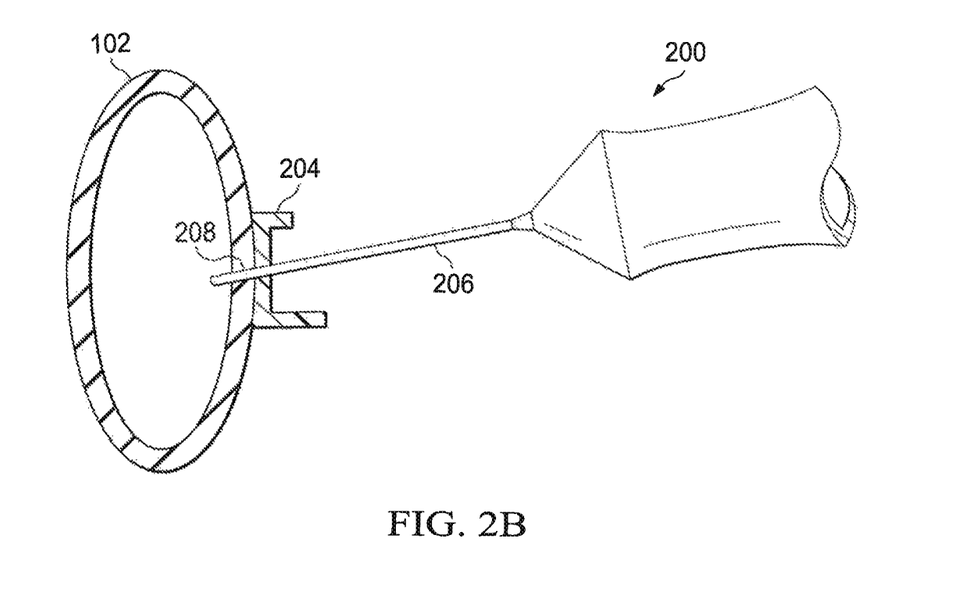

In FIG. 2B, a fluid-filled haptic 201 is shown depicting how needle tip 208 may be used when toroid portion 102 is deflated or evacuated. FIG. 2B is a sectional view with receiving feature 204 implemented as a C-groove that is self-sealing when a needle 206 penetrates receiving feature 204. For example, fluid-filled haptic 201 may be placed in an injector and injected into the eye, as shown in FIG. 2B. In some implementations, fluid-filled haptic 201 may be deflated or evacuated intraoperatively using needle 206 to remove the fluid that was previously filled in toroid portion 102.

Although receiving feature 104/204, as shown in FIGS. 1A, 1B, 2A, and 2C, has been depicted and described as including a recess for receiving and retaining the IOL optic, the present disclosure contemplates that the IOL optic may be received or retained using any suitable receiving or retaining feature that may physically engage and retain the IOL optic in a particular position within toroid portion 102. For example, in other implementations, the receiving or retaining feature of toroid portion 102 may include a protrusion (not shown) that mates with a corresponding recess formed in the IOL optic to hold the IOL optic in place. In another example implementation, the receiving or retaining feature may include a spring mechanism that exerts a force against the IOL optic when the IOL optic is placed in position within toroid portion 102, to hold the IOL optic in place. For example, the interior surface of toroid portion 102 may include a leaf spring or a leaf clip that is fixed at one end and provides radial compression of the IOL optic at the other end, and remains disposed between the IOL optic and the interior surface of toroid portion 102 when the IOL optic is installed to hold the IOL optic in place. It will be understood that various features and retaining mechanisms for the IOL optic may be combined or selected as desired in particular implementations.

Figure 2C:
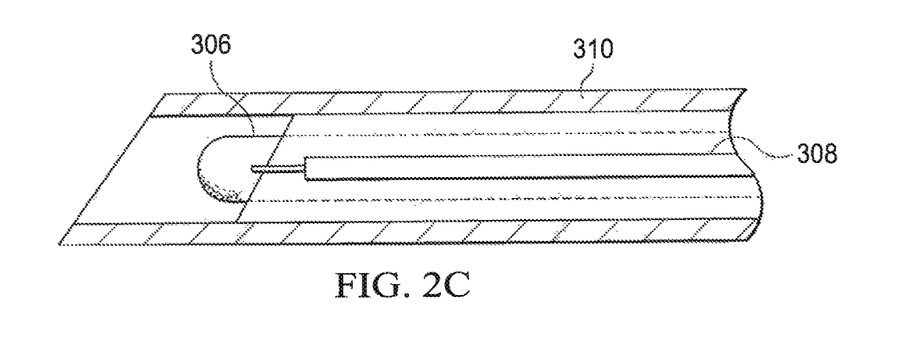

In FIG. 2C, an example of fluid-filled haptic 100 placed in an injector casing 310 shows how an IOL 306 with a fluid-filled haptic may be preloaded into the injector. As shown, IOL 306 is loaded into an injector casing 310 with a fluid line 308 attached, depicting an alternate implementation to the fluid-filling shown in FIGS. 2A and 2B. After filling, fluid line 308 may be removed intraoperatively.

Figure 3A:
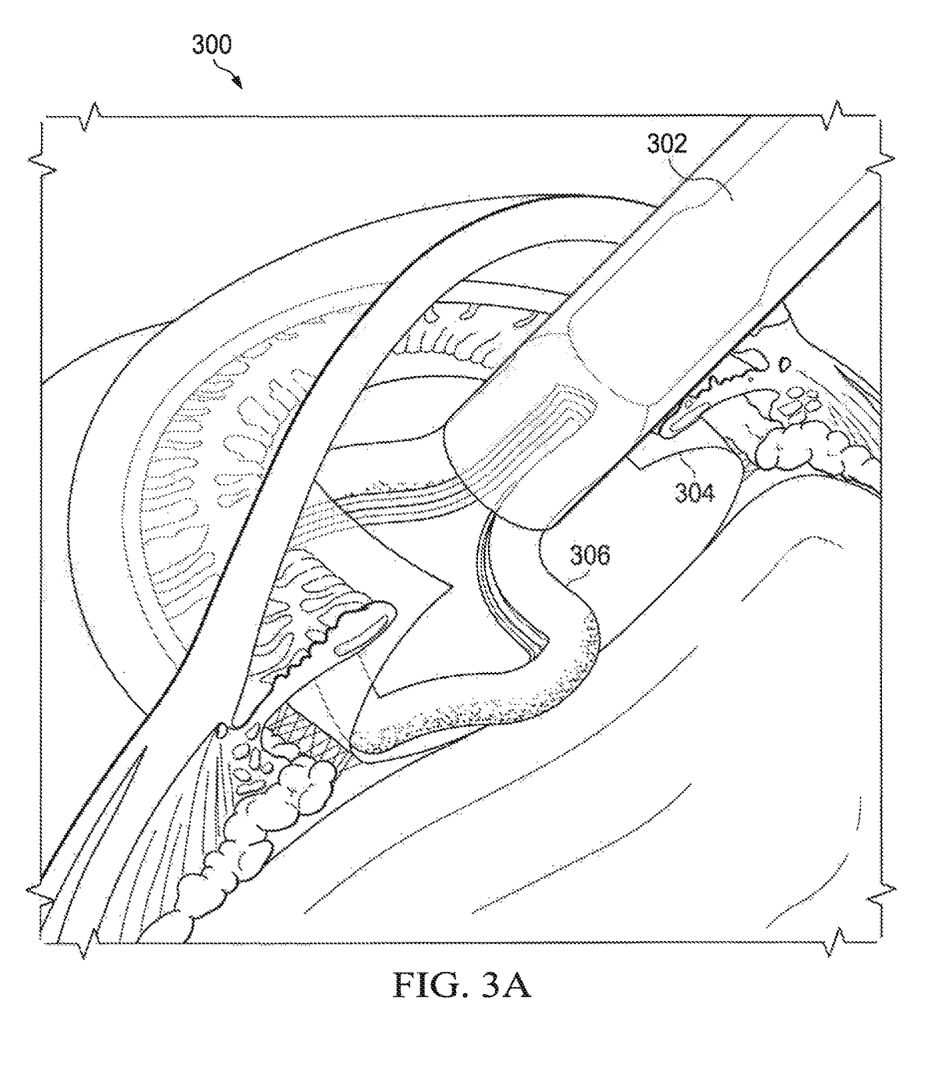
FIGS. 3A and 3B are depictions of implantation of an IOL with a fluid-filled haptic in an eye.

Referring now to FIG. 3A, an injection 300 of an IOL 306 with a fluid-filled haptic is depicted. In FIG. 3A, IOL 306 is shown being injected into a capsular bag 304 of an eye of a patient using an injector 302. The injector penetrates the cornea at an incision made for the surgical procedure, which may be as small as 2 mm in length. As shown in injection 300, IOL 306 is folded over for injection and may represent the two-piece embodiment with fluid-filled haptic 100 shown being injected first, which is followed by the injection of the IOL optic (not shown).

Figure 3B:
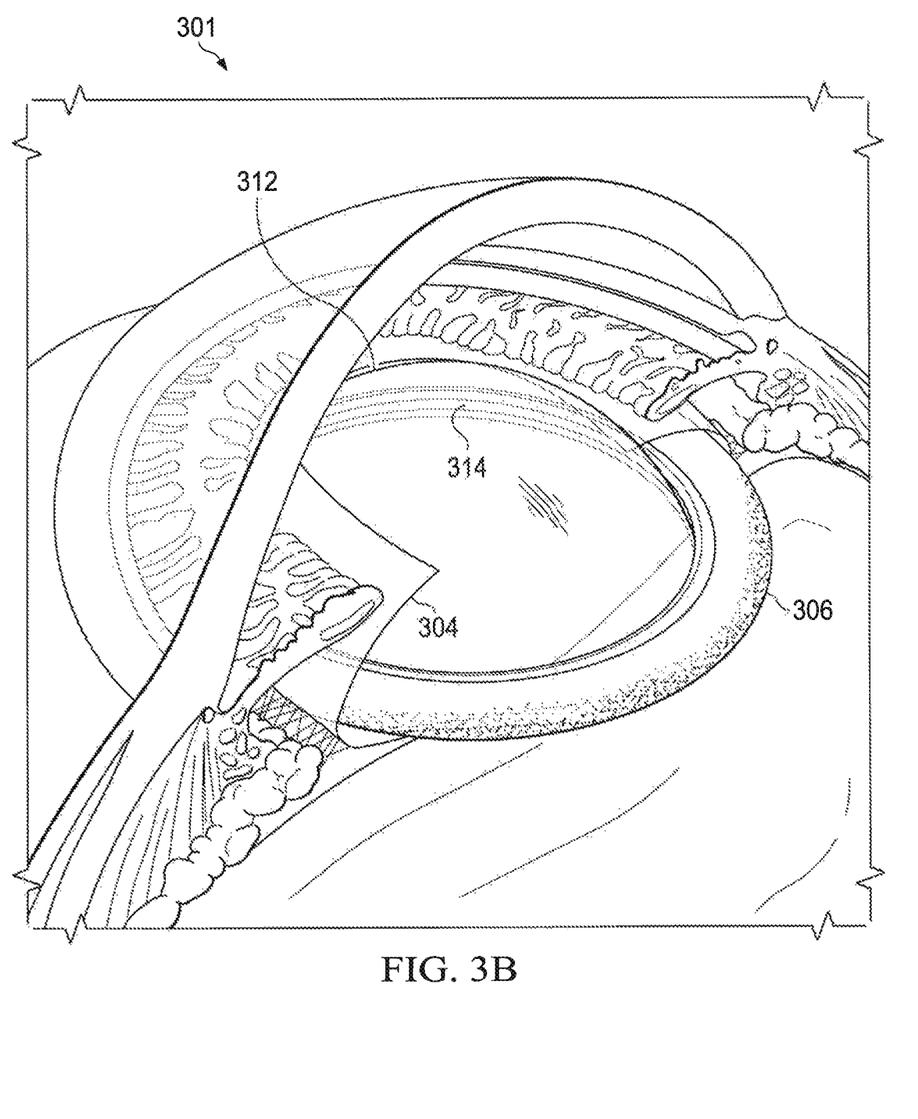

Referring now to FIG. 3B, an implant 301 of IOL 306 with a fluid-filled haptic is depicted postoperatively in capsular bag 304 of the eye of the patient. In FIG. 3B, an IOL optic 312 is shown placed within a receiving feature 314 of IOL 306, depicting how IOL 306 is postoperatively immobilized within capsular bag 304.

Figure 4:
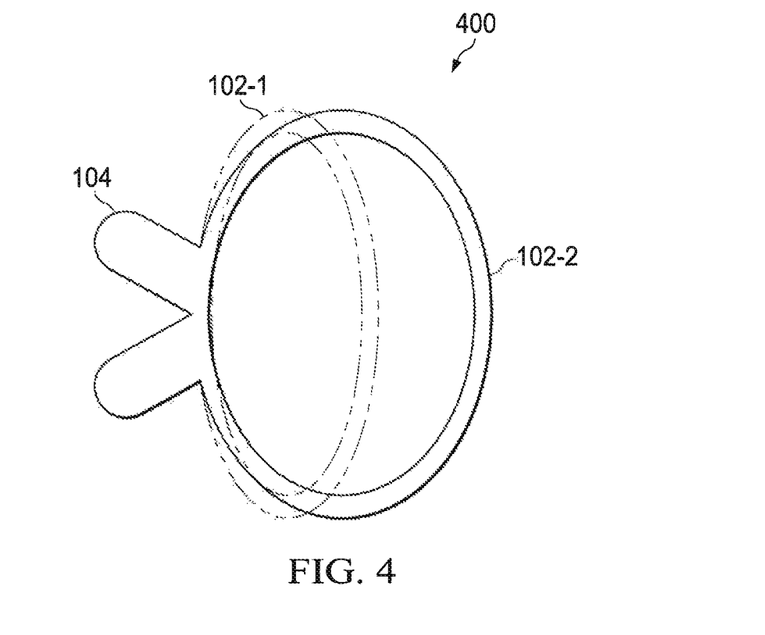
FIG. 4 is a depiction of a fluid-filled haptic for an IOL in cross-section.

Referring now to FIG. 4, a fluid-filled haptic 400 for an IOL is shown in cross-section having a receiving feature 104 that is a V-groove. In FIG. 4, a first toroid portion 102-1 shows a cross-section with little or no filling of the fluid, while a second toroid portion 102-2 shows how the shape of the cross-section changes with more or increased filling of the fluid. The change in cross-sectional shape of toroid portion 102 in FIG. 4 shows how fluid-filled haptic 400 can be fitted into capsular bag 304 individually for each patient using fluid filling.

Figure 5:
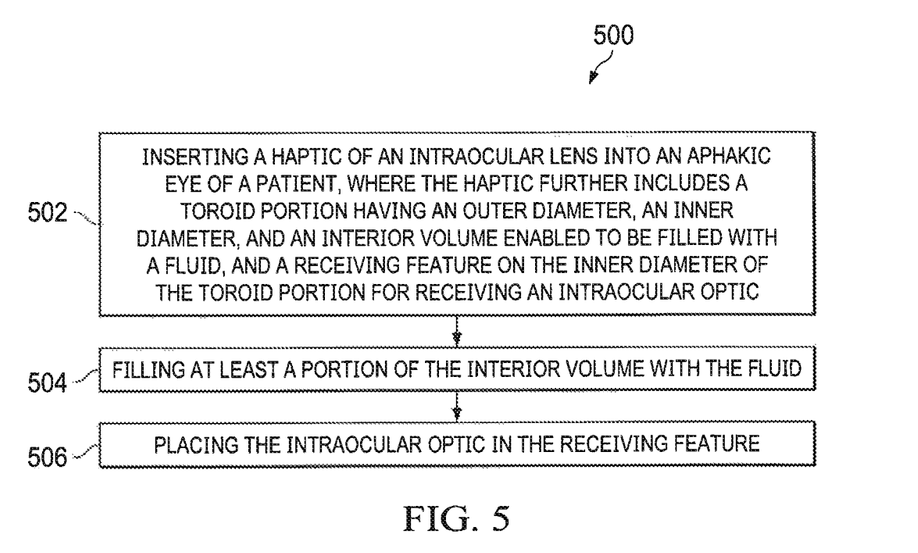
FIG. 5 is a flow chart of selected elements of a method for implanting an IOL having a fluid-filled haptic.

Referring now to FIG. 5, a flow chart of selected elements of an embodiment of a method 500 for implanting an IOL having a fluid-filled haptic, as disclosed herein. It is noted that certain operations described in method 500 may be optional or may be rearranged in different embodiments.

Method 500 may begin, at step 502, by inserting a haptic of an IOL into an aphakic eye of a patient, where the haptic further includes a toroid portion having an outer diameter, an inner diameter, and an interior volume configured to be filled with a fluid, and a receiving feature on the inner diameter of the toroid portion for receiving an IOL optic. At step 504, at least a portion of the interior volume is filled with the fluid. At step 506, the IOL optic is placed in the receiving feature. In the method, the receiving feature may be formed as a groove on at least a portion of the inner radius, the groove corresponding in size to a circumferential diameter of the IOL optic and extending circumferentially over at least a portion of the inner diameter, while placing the IOL optic in the receiving feature may further include placing the IOL optic in the groove. In method 500, filling at least a portion of the interior volume with the fluid may further include penetrating the receiving feature using a needle to enable the interior volume to be filled with the fluid using the needle, where the receiving feature is self-sealing to the fluid when the needle is removed. In method 500, inserting the haptic of the IOL into the aphakic eye of the patient may further include folding the toroid portion and the receiving feature in an injector, and using the injector to inject the haptic into the aphakic eye. In method 500, filling at least a portion of the interior volume with the fluid may further include filling the interior volume with the fluid until the outer diameter of the toroid portion circumferentially fits an equator of a capsular bag of the aphakic eye. In method 500, placing the IOL optic in the receiving feature may further include using a measuring instrument to determine a position of the toroid portion in the eye, and selecting the IOL optic based on the position of the toroid portion. Specifically, the measuring instrument may be used to determine or measure an exact position of the receiving feature, since the position of the receiving feature would be determinative for the postoperative position of the IOL optic.

As disclosed herein, an IOL utilizes a haptic formed as a toroid portion configured to fit into a capsular bag of an aphakic eye of a patient. The toroid portion may be separate from an IOL optic and may include a receiving feature for the IOL optic. The toroid portion may be configured for intraoperative fluid-filling for snug fitting at the equator of the capsular bag, in order to immobilize the IOL optic.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. An intraocular lens haptic comprising:
a toroid portion having an outer circumference, an inner circumference, and an interior volume, wherein the interior volume of the toroid portion is configured to be filled with a fluid that is configured to at least partially solidify; and
a receiving feature extending from an inner surface of the toroid portion for receiving an intraocular lens optic, wherein the receiving feature extends around at least half of the inner circumference of the toroid portion, the receiving feature configured for penetration by a needle to enable the interior volume to be filled with the fluid using the needle;
wherein the fluid comprises a base component and a curing agent adapted to be delivered to the interior volume of the toroid portion subsequent to delivery of the base component to the toroid portion, the curing agent configured to at least partially solidify the base component.

2. The intraocular lens haptic of claim 1, wherein the receiving feature comprises a first portion and a second portion extending from the inner surface of the toroid portion and forming a groove on at least a portion of the inner surface of the toroid portion, the groove corresponding in size to a circumference of the intraocular lens optic.

3. The intraocular lens haptic of claim 2, wherein the groove extends around the entire inner circumference of the toroid portion.

4. The intraocular lens haptic of claim 1, wherein the curing agent is further configured to cause the fluid to at least partially solidify in response to exposure to ultraviolet light.

5. The intraocular lens haptic of claim 1, wherein the receiving feature is self-sealing when the needle is removed.

6. The intraocular lens haptic of claim 1, wherein the outer circumference of the toroid portion is configured to circumferentially fit an equator of a capsular bag when the interior volume is filled with the fluid.

7. An intraocular lens, comprising:
a haptic comprising:
a toroid portion having an outer circumference, an inner circumference, and an interior volume, wherein the interior volume of the toroid portion is configured to be filled with a fluid that is configured to at least partially solidify; and
a receiving feature extending from an inner surface of the toroid portion,
the receiving feature configured for penetration by a needle to enable the interior volume to be filled with the fluid using the needle, wherein the receiving feature extends around at least half of the inner circumference of the toroid portion;
wherein the fluid comprises a base component and a curing agent adapted to be delivered to the interior volume of the toroid portion following delivery of the base component to the toroid portion, the curing agent configured to solidify the base component; and
an intraocular lens optic configured to fit in the receiving feature when the intraocular lens is implanted into an eye of a patient.

8. The intraocular lens of claim 7, wherein the receiving feature comprises a first portion and a second portion extending from the inner surface of the toroid portion and forming a groove on at least a portion of the inner surface of the toroid portion, the groove corresponding in size to a circumference of the intraocular lens optic and extending around at least a portion of the inner circumference.

9. The intraocular lens of claim 7, wherein the curing agent is further configured to cause the fluid to at least partially solidify in response to exposure to ultraviolet light.

10. The intraocular lens of claim 7, wherein the receiving feature is self-sealing when the needle is removed.

11. The intraocular lens of claim 7, wherein the outer circumference of the toroid portion is configured to circumferentially fit an equator of a capsular bag of the eye when the interior volume is filled with the fluid.

12. The intraocular lens of claim 7, wherein the intraocular lens optic is attached to the receiving feature.

13. The intraocular lens haptic of claim 2, wherein the groove comprises a V-shaped groove.

14. The intraocular lens haptic of claim 1, wherein the receiving feature comprises a C-shaped groove.

15. The intraocular lens haptic of claim 1, wherein the receiving feature comprises a compressible element.

16. A method for implanting intraocular lenses, the method comprising:
inserting a haptic of an intraocular lens into an aphakic eye of a patient, wherein the haptic comprises:
a toroid portion having an outer circumference, an inner circumference, and an interior volume, wherein the interior volume of the toroid portion is configured to be filled with a fluid that is configured to at least partially solidify; and
a receiving feature extending from an inner surface of the toroid portion for receiving an intraocular lens optic, wherein the receiving feature extends around at least half of the inner circumference of the toroid portion, the receiving feature configured for penetration by a needle to enable the interior volume to be filled with the fluid using the needle;
wherein the fluid comprises a base component and a curing agent adapted to be delivered to the interior volume of the toroid portion subsequent to delivery of the base component to the toroid portion, the curing agent configured to at least partially solidify the base component;
filling at least a portion of the interior volume with the fluid; and
placing the intraocular lens optic in the receiving feature.

17. The method of claim 16, wherein:
the receiving feature forms a groove on at least a portion of the inner surface of the toroid portion,
the groove corresponds in size to a circumference of the intraocular lens optic and extends around at least half of the inner surface of the toroid portion, and
wherein placing the intraocular lens optic in the receiving feature comprises placing the intraocular lens optic in the groove.

18. The method of claim 16, wherein filling at least the portion of the interior volume with the fluid comprises penetrating the receiving feature using the needle to enable the interior volume to be filled with the fluid using the needle, wherein the receiving feature is self-sealing to the fluid when the needle is removed.

19. The method of claim 16, wherein filling at least the portion of the interior volume with the fluid comprises filling the interior volume with the fluid until the outer circumference of the toroid portion circumferentially fits an equator of a capsular bag of the aphakic eye.

20. The method of claim 16, wherein placing the intraocular lens optic in the receiving feature comprises:

using a measuring instrument to determine a position of the toroid portion in the aphakic eye; and selecting the intraocular lens optic based on the position of the toroid portion.

* * * * *